(12) United States Patent
Thomas et al.

(10) Patent No.: US 7,757,697 B2
(45) Date of Patent: Jul. 20, 2010

(54) METHOD FOR REDUCING NITROSAMINES IN TOBACCO

(75) Inventors: Terry Thomas, Jacksonville, FL (US); John Brandon, Hopkinsville, KY (US); William A. Bailey, Princeton, KY (US); Thomas A. Losty, Jacksonville, FL (US)

(73) Assignees: Swisher International, Inc., Jacksonville, FL (US); University of Kentucky Research Foundation, Lexington, KY (US)

( * ) Notice: Subject to any disclaimer, the term of this patent is extended or adjusted under 35 U.S.C. 154(b) by 396 days.

(21) Appl. No.: 11/610,121

(22) Filed: Dec. 13, 2006

(65) Prior Publication Data

US 2007/0149408 A1 Jun. 28, 2007

Related U.S. Application Data

(60) Provisional application No. 60/753,683, filed on Dec. 22, 2005.

(51) Int. Cl.
*A24B 15/00* (2006.01)
*A24B 15/18* (2006.01)
*A24B 15/28* (2006.01)

(52) U.S. Cl. .................. 131/310; 131/290; 131/300; 131/309

(58) Field of Classification Search ............ None
See application file for complete search history.

(56) References Cited

U.S. PATENT DOCUMENTS

| | | | | |
|---|---|---|---|---|
| 3,958,580 A | * | 5/1976 | Mergens et al. | 131/352 |
| 5,762,936 A | * | 6/1998 | Ronzio et al. | 424/757 |
| 6,150,408 A | * | 11/2000 | Nair et al. | 514/532 |
| 2005/0121046 A1 | * | 6/2005 | Hempfling et al. | 131/347 |

FOREIGN PATENT DOCUMENTS

WO   WO 2004068973 A2 * 8/2004

OTHER PUBLICATIONS

Rundolf, Torgny et al. Potential Nitrite Scavengers as Inhibitors of the Formation of N-Nitrosamines in Solution and Tobacco Matrix Systems. J. Agric. Food Chem. vol. 48 pp. 4381-4388. Aug. 23, 2000.*

* cited by examiner

*Primary Examiner*—Russell Kallis
(74) *Attorney, Agent, or Firm*—Lucas & Mercanti, LLP

(57) ABSTRACT

Nitrosamines are reduced in tobacco by treating a whole tobacco leaf with ferulic acid. Treatment is conducted by applying an aqueous solution of ferulic acid to the whole tobacco leaf immediately before, at, or after harvesting, or fire curing the whole tobacco leaf with wood smoke containing the ferulic acid.

17 Claims, No Drawings

METHOD FOR REDUCING NITROSAMINES IN TOBACCO

Priority of U.S. Patent Application No. 60/753,683, filed Dec. 22, 2005 is claimed and the same is incorporated herein by reference.

BACKGROUND OF THE INVENTION

1. Field of Invention

This Invention relates to tobacco and, more specifically, to a method for reducing nitrosamines in tobacco.

2. Related Art

Nitrosamines, sometimes referred to as N-nitrosamines, are believed to form on tobacco leaves during the curing process of harvested tobacco leaves. Nitrosamines that form on tobacco are generally referred to as tobacco specific nitrosamines (TSNA) and are believed to be the result of a chemical reaction between tobacco alkaloids and oxides of nitrogen, more specifically, nitrites.

Green tobacco, or tobacco prior to harvesting and immediately after harvesting, is known to contain virtually no nitrosamines. In air-cured tobacco, the appearance of nitrosamines occurs at the end of yellowing, about 14 days into curing. The reaction between the oxides of nitrogen and the tobacco alkaloids which are generally amines are believed to be caused by the presence of bacteria which occur naturally on the leaves. These bacteria contain enzymes referred to as nitrate reductase. The enzyme is thought to convert the naturally occurring nitrate to nitrite under anaerobic conditions.

It is known that certain compounds when added to ground, air-cured tobacco in solution and incubated for a period of time, can inhibit the formation of nitrosamines. Included in these compounds is ferulic acid.

Conventionally, tobacco is harvested by cutting the stalks of tobacco in the field or plucking the whole leaves from the stalks as they become ripe. After harvesting, the leaves or stalks which bear the leaves are cured by drying, typically in an aerated barn, for a period of 1 to 6 weeks at a temperature of 20 to 70° C. After curing, the leaves are fermented by storing them for an extended period of time at a somewhat elevated temperature. Some tobacco is cured with smoke, such tobacco is referred to as Dark Fire Cured or Fire Cured Tobacco.

Nitrosamines are alleged as being carcinogenic and it is desirable to reduce nitrosamines in cured tobacco.

SUMMARY OF THE INVENTION

It has now been discovered that nitrosamines in cured tobacco can be reduced by treating the whole tobacco leaf with a ferulic acid compound. Treatment is conducted at the time of harvesting by applying an aqueous solution of the ferulic acid compound to the whole tobacco leaf; or at the time of fire curing by applying smoke containing the ferulic acid compound to the whole tobacco leaf as it is fire cured. For fire cured tobacco, the whole tobacco leaf can be treated at both times, at harvesting and at fire curing.

It has further been discovered that the presence of the ferulic acid compound on the tobacco has no effect on the overall curing and fermentation processes which are subsequently conducted on the tobacco, except for the reduction of nitrosamines. Ferulic acid is generally recognized as safe and thus there is no need to further treat the tobacco to remove the ferulic acid compound.

The process of the present Invention can be defined as a method for treating tobacco to inhibit formation of nitrosamines in the tobacco leaf comprising:
 treating a whole tobacco leaf with a ferulic acid compound; and
 recovering said treated whole tobacco leaf.

The phrase whole tobacco leaf means that the plant is fully matured, ready for harvesting or harvested and the leaf is still intact.

In one preferred embodiment, the treatment is conducted by applying an aqueous solution of a ferulic acid compound to the whole tobacco leaf between immediately before and immediately after harvesting the tobacco from the field.

In another preferred embodiment, the treatment is conducted by applying a smoke containing the ferulic acid compound to the whole tobacco leaf during fire curing. Preferably, the smoke is a wood smoke, i.e. a smoke generated by burning wood, and especially sawdust during the fire curing process.

Treating the whole tobacco leaf with the aqueous solution of the ferulic acid compound can be conducted while the whole tobacco leaf is on the stalk, or on the tobacco leaf which has been harvested by removing the tobacco leaf from the stalk. Treating the whole tobacco leaf on the stalk is conducted immediately before, at, or after harvesting from the field and before curing. Treating the whole tobacco leaf which has been removed from the stalk is conducted immediately after it has been harvested from the field and prior to curing.

The aqueous solution comprises:
 an effective amount of a ferulic acid compound and water.

The effective amount of the ferulic acid compound is effective to inhibit the production of nitrosamines in the tobacco.

The term "ferulic acid compound", as used in the Specification and Claims, means ferulic acid and esters of ferulic acid.

The aqueous solution can also comprise an alcohol and/or a surfactant.

Applying the aqueous solution is suitably conducted by spraying the aqueous solution onto the whole tobacco leaf in the field at harvesting or immediately before harvesting, or immediately after harvesting. Applying the aqueous solution can be also conducted immediately after harvesting by dipping the whole tobacco leaf either by itself or on a stalk into the aqueous solution.

In another preferred embodiment, treating is conducted during fire curing of the whole tobacco leaf by applying a smoke containing a ferulic acid compound to the tobacco to cure the tobacco. Treating can be done by placing a dry ferulic acid compound onto the wood, e.g. sawdust, used to generate the smoke during fire curing. Preferably, the ferulic acid compound is added on top of the sawdust at the start of the fire curing while the leaf is still somewhat green. The ferulic acid compound can be added to the sawdust throughout the fire curing. Care must be taken not to place the ferulic acid compound directly into the fire. The ferulic acid compound should be placed on top of the sawdust so that the ferulic acid compound is either vaporized or sublimated and is carried by the wood smoke during the curing to the tobacco leaf. The ferulic acid will burn if it comes into direct contact with the flame.

DETAILED DESCRIPTION OF THE INVENTION

Ferulic acid ($C_{10}H_{10}O_4$) also known as 4-hydroxy-3-methoxy cinnamic acid is conventionally available as a powder. Any conventional source of ferulic acid is suitable for use in the present Invention. Esters of ferulic acid are also suitable for use in the present Invention and, specifically, ethyl ester, ethyl ferulate, and ethyl-4-hydroxy-3-methoxy cinnamic acid. Any conventional source of an ester of ferulic acid is suitable for use in the present Invention. Typically, ferulic acid and the ester of ferulic acid are commercially available in a solid form, as a granular product. The ferulic acid compound is ferulic acid, an ester of ferulic acid or a combination of the acid and ester.

It is generally found that in order to form the aqueous solution, alcohol is needed to dissolve the solid ferulic acid compound in solution, although hot water can also be used to dissolve the ferulic acid compound in the aqueous solution. Suitable alcohols include ethanol, methanol, and propanol, however, ethanol is preferred because it is safe and need not be removed from the tobacco. Suitably, the amount of alcohol used is about 1% to about 20% by weight solution and, more preferably, about 10% by weight solution of alcohol. For example, with ethanol, five (5) gallons of ethanol per 250 gallons of water works well. This will give a 2% solution.

Suitably, the amount of ferulic acid compound present in the aqueous solution is about 0.1 to about 1% weight by volume, more suitably, about 0.2 to about 0.6% weight by volume, and good results have been obtained with about 0.25% weight by volume and about 0.5% weight by volume. These percentages are based on the grams of solid ferulic acid compound to milliliters of water.

Suitably, a surfactant is used in the aqueous solution in order to help adhere the ferulic acid compound to the tobacco leaf and assist in the absorption of the ferulic acid compound by the tobacco leaf. Any conventional source of surfactants can be employed in the present Invention. Suitable surfactants include INDUCE™, TOP SURF™, DE-FACT™ 820 and X-77™. Good results have been obtained with INDUCE™. INDUCE™ is a non-ionic surfactant obtained from Helena Chemical Company which is identified as a blend of alkyl aryl polyoxylkane ether and free fatty acids in aqueous solution. TOP SURE™ is an anionic-ionic surfactant obtained from Agrilliance and is identified as a blend of alkylpolyethoxylkene ethers and other ethoxylated derivatives. DE-FAC™ 820 is a non-ionic surfactant comprising 80% alkyl and alkylaryl polyoxyethyi-ene glycoi manufactured for Southern States Cooperative Inc. of Richmond, Va. X-77™ is a blend of an alkyiarylpolyoxyethylene, alkylpolyoxyethylenyl, fatty acids, glycols and dimethylpolysiloxane. X-77™ is available from Loveland Industries, Inc. of Greely, Colo.

The amount of surfactant employed in the aqueous solution is suitably about 0.1% to about 0.5% by volume and, more preferably, about 0.2% to about 0.3% volume to volume. Good results have been obtained in an amount of about 0.25% by volume.

A conventional source of water is suitable for making up the aqueous solution. If hot water, about 120° F. (50° C.) water is used, alcohol is not needed to dissolve the ferulic acid compound.

Mixing of the components to form the aqueous solution is done in a conventional manner using conventional equipment.

When treating by methods of spraying the aqueous solution on the tobacco in the field at or before harvesting, about 25 to about 75 gallons per acre (25 to 75 ml/m$^2$) of aqueous solution are sprayed onto the tobacco. More suitably, about 40 to about 60 gallons per acre (40 to 60 ml/m$^2$) of aqueous solution are applied to the tobacco. Good results have been obtained by applying about 50 gallons per acre (50 ml/m$^2$) of aqueous solution during spraying of the tobacco on the stalk in the field at or before harvesting. Additionally, good results have been obtained by applying about 100 ml of solution per stalk. Alternatively, about 0.01 ml per square inch of tobacco leaf.

In treating the tobacco leaf or the tobacco on the stalk by dipping into an aqueous solution in accordance with the present Invention, suitably the whole leaf or the whole stalk is submerged and then removed from the aqueous solution. Such dipping must be conducted in order to wet the tobacco leaf on all sides.

In order to spray the aqueous solution on the whole tobacco leaf in the field at or before harvesting, any conventional apparatus and method for spraying agricultural crops can be employed.

Spraying of the harvested whole tobacco leaf can be conducted in any conventional manner using conventional equipment.

Suitable means for dipping the tobacco into an aqueous solution employ any conventional method and any conventional machinery such as a conveyor belt which moves the whole leaf tobacco through a bath of the aqueous solution.

In any case, the aqueous solution is constantly agitated to help keep the ferulic acid compound in solution.

Suitably, the whole tobacco leaf is treated with the aqueous solution between about 75 hours before harvesting and about 75 hours after harvesting. Preferably, the tobacco leaf is treated between about 50 hours before harvesting and 50 hours after harvesting and, more preferably, about 30 hours before to 30 hours after harvesting. From a more conventional standpoint, this means treating the whole tobacco leaf between about three days before harvesting and about three days after harvesting. Preferably, the tobacco leaf is treated before harvest. The ferulic drys and adheres onto the leaf after treatment with the aqueous solution.

Curing of the tobacco treated with the aqueous solution in accordance with the present Invention is conducted in a conventional manner using conventional equipment. Normally, the stalks of tobacco containing the leaves are hung in a barn at atmospheric pressure and temperature with air flowing through the barn for a period of 1 to 6 weeks. Curing can also be conducted by forcing air through the barn so as to increase the volume of air which passes over the tobacco leaf. The tobacco can also be fire cured with smoke.

Treating the whole leaf tobacco during fire curing, means adding a ferulic acid compound to the smoke during fire curing. Suitably, this is done by adding a solid ferulic acid compound to the wood during the fire curing process. Preferably, the ferulic acid compound is added to the wood at the beginning of the fire curing. The smoke from the wood as it smolders carries the ferulic acid compound to the whole leaf in the same way the smoke is carried to the leaf.

Suitably about one pound of a dry ferulic acid compound is added on top of the wood to treat one acre of whole tobacco in a barn during fire curing. An acre of tobacco in a barn is about 5000 stalks with 16 to 20 leaves per stalk.

Any type of tobacco leaf can be employed in the present Invention, such as, flue cured, Burley, fire cured, Maryland and cigar wrapper. Good results have been obtained with dark fire cured tobacco varieties, Narrow leaf Madole, and VA 309 tobacco.

Fermentation and further processing of the treated, cured tobacco is conducted in a conventional manner using conventional equipment.

The resulting cured tobacco has been found to have substantially less nitrosamines compared to cured tobacco which had not been treated in accordance with the present Invention. Specifically, Applicant has found a reduction on the order of about 15% to about 85% of nitrosamines between the untreated cured tobacco and treated cured tobacco.

These and other aspects of the present Invention may become more readily apparent from one or more of the following examples which are hereby presented for purposes of illustration.

Example 1

This example illustrates the reduction in nitrosamines in cured tobacco obtained with the present Invention where the whole green leaf is treated immediately after harvesting.

Two samples of whole tobacco leaves still on the stalk were cured in a bulk barn. One sample was treated with ferulic acid by spraying an aqueous solution comprising 0.25% wt. by volume of ferulic acid onto the harvested tobacco plant, one day after harvesting. The amount of solution applied to each stalk of leaves was 100 ml. The other sample was untreated tobacco of the same variety as the treated tobacco and harvested at the same time as the treated tobacco.

Both the treated and untreated samples were hung in the same bulk barn to cure. The curing process comprised two weeks of circulating air throughout the bulk barn followed by three weeks of wood fire curing.

After curing, whole tobacco leaves were randomly removed from the stalk and subject to testing to determine the content of nitrosamines. The nitrosamines that were measured were N-nitrosonornicotine (NNN), N-nitrosoanatabine (NAT), N-nitrosoanabasine (NAB), and 4-methyl-N-nitrosamine-1-(3-pyridyl)-1-butanone (NNK). The total content of NNN, NAT, NAB, and NNK make up the total N-nitrosamine (TSNA) content. The methodology employed was a chromatographic method described by Risner, Reece and Morgan, Recent Advances in Tobacco Science 27:47 (2001). The results of these tests are reported in Table 1.

TABLE 1

| | Total TSNA (dwb), ppm | | | |
|---|---|---|---|---|
| Sample | Lug | Second | Leaf | Avg. |
| Untreated | 2.43 | 1.60 | 2.16 | 2.14 |
| Treated | 1.84 | 1.37 | 1.64 | 1.59 |

As can be seen, the process of the present Invention reduced the nitrosamines in the cured tobacco by about 15% to about 25%.

As is known to those of skill in the art, the term "Lug" is used to refer to lower leaves, the term "Second" is used to refer to the middle leaves and the term "leaf" is used to refer to the top leaves of the stalk.

Example 2

This example illustrates the reduction in nitrosamines in cured tobacco with the present Invention where the whole green leaf is treated before harvesting.

Two samples of whole leaf tobacco still on the stalk, were cured in a bulk barn. One sample was treated with ferulic acid by spraying an aqueous solution comprising 0.25% wt. by Vol. ferulic acid and 0.25% by volume surfactant, INDUCE™. The solution was sprayed onto tobacco in the field, one day prior to harvesting the tobacco in an amount of 50 gallons per acre (approximately 5000 plants per acre). The other sample was untreated tobacco of the same variety as the harvested tobacco and harvested at the same time as the treated tobacco.

Both samples were hung and cured in the same bulk barn. The curing process comprised two weeks of circulating air throughout the bulk barn followed by two weeks of wood fire curing. During curing, the temperatures in the barn ranged from 7 to 57° C. and the relative humidity ranged from 20 to 95%.

After curing, tobacco leaves were randomly removed from the stalk and tested for nitrosamines in the same manner as Example 1. The results of these tests are shown in Table 2.

TABLE 2

| | Total TSNA (dwb), ppm | | | |
|---|---|---|---|---|
| Sample | Lug | Second | Leaf | Avg. |
| Untreated | 3.19 | 2.61 | 2.43 | 2.74 |
| Treated | 2.25 | 0.61 | 0.42 | 1.09 |

As can be seen from Table 2, the treated tobacco had a reduced nitrosamine content from about 30% to about 85%.

Example 3

This example illustrates the reduction in nitrosamines in cured tobacco with the present Invention where the whole tobacco leaf is treated with two different concentrations of ferulic acid in solution, both being treated before harvesting.

Three samples of whole leaf tobacco still on the stalk were cured in a bulk barn. One sample (treated 0.25%) was treated by spraying an aqueous solution comprising 0.25% wt. by vol. ferulic acid and 0.25% surfactant (INDUCE™) onto the tobacco plant 24 hours prior to harvesting. The amount of solution applied to the first sample was 50 gallons per acre. The second sample (treated 0.50%) was treated by spraying an aqueous solution comprising 0.5% wt. by vol. ferulic acid and 0.25% surfactant (INDUCE™) onto the tobacco plant 24 hours prior to harvesting. The amount of solution applied to the second sample was 50 gallons per acre. The third sample was untreated. All three samples were the same variety of tobacco and were harvested at the same time.

All three samples were cured in the same bulk barn under the same conditions. All three samples were cured for two weeks with air circulated through the barn followed by two weeks of wood fire curing. During curing, the temperatures in the barn ranged from 7 to 57° C. and the relative humidity ranged from 20 to 95%.

After curing, tobacco leaves were randomly removed from the stalk and tested for nitrosamines in the same manner as Example 1. The results of these tests are shown in Table 3.

TABLE 3

| | Total TSNA (dwb), ppm | | | |
|---|---|---|---|---|
| Sample | Lug | Second | Leaf | Avg. |
| Untreated | 2.93 | 1.26 | 1.25 | 1.81 |
| Treated, 0.25% | 1.11 | 0.71 | 0.71 | 0.84 |
| Treated, 0.50% | 1.18 | 0.98 | 0.76 | 0.97 |

As can be seen from Table 3, increasing the amount of ferulic acid in the solution did not have an increased affect on the reduction of nitrosamines. Also, it can be seen that the process of the present Invention reduced the nitrosamines by about 40% to about 65%.

Example 4

This example illustrates treating the whole leaf tobacco with an aqueous solution comprising ferulic acid, ethanol and a surfactant, two days prior to harvest.

Tobacco plants were treated by spraying them in the field with an aqueous solution comprising 0.25% wt. by vol. of ferulic acid, 5 gallons ethanol (95%), 250 gallons water and 0.25% by vol. of a non-ionic surfactant (DE FAC 820). This gave a 2% ethanol solution. Fifty (50) gallons of aqueous solution was applied per acre for the treated plants.

Treated and non-treated tobacco was harvested and cured in a conventional dark fire tobacco barn with manual vents for aeration for 6 weeks, one week of natural ventilation followed by five weeks of wood fire curing in a conventional manner. The curing was conducted in a conventional curing barn as is typically found in the dark tobacco production regions of Kentucky and Tennessee. Both the treated and untreated tobacco were the same variety and harvested at the same time.

Random leaves were removed from the cured treated and cured untreated tobacco and TSNA was measured in accordance with Example 1. The test results are reported in Table 4, below.

TABLE 4

| Sample | Total TSNA (dwb), ppm |
|---|---|
| Untreated | 58 |
| Treated | 11 |

As can be seen, the treatment resulted in an 85% reduction in TSNA.

Example 5

This example illustrates that a surfactant alone does not reduce the nitrosamine level in tobacco and that the present Invention is synergistic.

Tobacco plants were treated by spraying them with an aqueous solution of 0.25% by Vol. non-ionic surfactant (IN-DUCE) in an amount of 50 gallons per acre, 24 hours before harvest. No ferulic acid was included in the treatment.

Treated and non-treated tobacco of the same variety were then harvested at the same time and cured in a barn by two weeks of circulating air followed by two weeks of wood fire curing.

Random leaves were removed from the cured treated and cured untreated tobacco and TSNA was measured in accordance with Example 1. The test results are reported in Table 5, below.

TABLE 5

| Sample | Total TSNA (dwb), ppm | | | |
|---|---|---|---|---|
| | Lug | Second | Leaf | Avg. |
| Untreated | 4.55 | 4.13 | 3.77 | 4.15 |
| Treated, INDUCE only | 5.98 | 5.02 | 4.98 | 5.33 |

As can be seen, the use of a surfactant did not reduce nitrosamines; in fact, nitrosamines were higher for the tobacco treated with the surfactant.

The combination of ferulic acid with a surfactant can be seen as synergistic because the combination of ferulic acid and surfactant reduces TSNA by 30 to 85% (Tables 2, 3 and 4) while the use of surfactant alone increases TSNA by 25% (Table 5) and the use of ferulic acid alone decreases TSNA by 15 to 25% (Table 1). Based on this data, it would be expected that the surfactant would counteract the ferulic acid to result in a 0% reduction in TSNA, rather than a decrease in TSNA.

Example 6

This example illustrates treating the whole tobacco leaf during fire curing with ferulic acid by adding the ferulic acid to the smoke used to cure the leaf.

In a conventional dark fire tobacco barn, wood lumber was laid on the floor of the barn and sawdust was spread on top of the wood. The lumber was set on fire and the sawdust smoldered and generated wood smoke. Ferulic acid, solid granular, from a conventional source, was sprinkled over the top of the sawdust at the start of the fire curing process and was applied in an amount of one pound per acre of tobacco in the barn, about 5000 tobacco plants. The fire curing started one or two days after the tobacco was harvested and hung in the barn. The ferulic acid lasted about one week on the sawdust during the fire curing.

It is believed that the ferulic acid sublimated or volatilized and was carried by the wood smoke to the tobacco leaves.

The fire curing was conducted for a total of 40 days.

After curing, random leaves were collected from the treated tobacco and from the untreated tobacco. Both treated and untreated tobacco were of the same variety and came from two different barns. The untreated tobacco came from a different barn but was fire cured in the same manner as the treated tobacco except for the ferulic acid treatment. Tests to determine the TSNA were conducted as in Example 1, and the results are reported in Table 6, below.

TABLE 6

| Sample | TSNA (Avg) (dwb), (ppm) |
|---|---|
| Untreated | 23 |
| Treated | 15 |

As can be seen, there was a 35% reduction in TSNA.

It will be understood that the claims are intended to cover all changes and modifications of the preferred embodiments of the Invention herein chosen for the purposes of illustration which do not constitute a department from the spirit and scope of the Invention.

What is claimed is:

1. A method of reducing the formation of nitrosamines in a cured tobacco comprising:
   applying an aqueous solution containing a ferulic acid compound on a whole tobacco leaf, prior to curing; and
   curing said whole tobacco leaf.

2. The method of claim 1, wherein the aqueous solution of said ferulic acid compound is applied on the whole tobacco leaf between immediately before to immediately after harvesting of the tobacco plant, but prior to curing.

3. The method of claim 2, wherein said applying is conducted by dipping said whole tobacco leaf in a bath of said aqueous solution after harvesting or by spraying said aqueous solution onto said whole tobacco leaf between immediately before to immediately after harvesting.

4. The method of claim 2, wherein said applying is conducted between about three days before harvesting and about three days after harvesting.

5. The method of claim 2 wherein the ferulic acid compound is ferulic acid, an ester of ferulic acid, or both, and said aqueous solution comprises said ferulic acid compound, a surfactant and water.

6. The method of claim 2, wherein said aqueous solution comprises said ferulic acid compound in an amount of about 0.1% to about 1% weight by volume, a surfactant and water.

7. The method of claim 2, wherein said aqueous solution is applied to said whole tobacco leaf prior to harvest in an amount of about 50 gallons per acre.

8. The method of claim 2, wherein said aqueous solution is applied to said whole tobacco leaf in an amount of about 0.01 ml per square inch of leaf.

9. The method of claim 5, wherein said aqueous solution further comprises an alcohol.

10. The method of claim 6, wherein said aqueous solution comprises said ferulic acid compound in an amount of about 0.2 to about 0.6% weight by volume.

11. The method of claim 6, wherein said aqueous solution comprises said ferulic acid compound in an amount of about 0.25 to about 0.5% weight by volume.

12. The method of claim 6, wherein said aqueous solution comprises said surfactant in an amount of about 0.1 to about 0.5% weight by volume.

13. The method of claim 6, wherein said aqueous solution comprises said surfactant in an amount of about 0.2 to about 0.3% weight by volume.

14. The method of claim 9, wherein said aqueous solution comprises said alcohol in an amount of about 1 to about 20% weight by volume.

15. The method of claim 14, wherein said aqueous solution comprises said alcohol in an amount of about 1 to about 10% weight by volume.

16. The method of claim 6, wherein said aqueous solution comprises 0.25% weight by volume of said ferulic acid compound and 0.25% weight by volume of said surfactant.

17. The method of claim 16, wherein said aqueous solution further comprises a 2% ethanol solution.

* * * * *